(12) United States Patent
Maier et al.

US007931921B2

(10) Patent No.: US 7,931,921 B2
(45) Date of Patent: Apr. 26, 2011

(54) METHOD OF SUBSTANTIALLY PREVENTING OR INHIBITING SUMMER BENTGRASS DECLINE

(76) Inventors: Frederick P. Maier, Farmerville, LA (US); William T. Hinton, Ruston, LA (US)

(*) Notice: Subject to any disclaimer, the term of this patent is extended or adjusted under 35 U.S.C. 154(b) by 933 days.

(21) Appl. No.: 11/676,098

(22) Filed: Feb. 16, 2007

(65) Prior Publication Data

US 2008/0207450 A1    Aug. 28, 2008

(51) Int. Cl.
*A01N 59/04* (2006.01)
*A01G 7/02* (2006.01)

(52) U.S. Cl. .................... 424/700; 504/119; 405/43

(58) Field of Classification Search .............. 424/700; 504/119; 405/43
See application file for complete search history.

(56) References Cited

U.S. PATENT DOCUMENTS

| | | | |
|---|---|---|---|
| 1,908,164 A * | 5/1933 | Minor | 71/1 |
| 4,015,366 A | 4/1977 | Hall | |
| 4,073,089 A | 2/1978 | Maginnes et al. | |
| 4,689,067 A | 8/1987 | Kuckens et al. | |
| 5,128,035 A | 7/1992 | Clack et al. | |
| 5,336,661 A | 8/1994 | Lucas | |
| 5,409,508 A | 4/1995 | Erickson | |
| 5,496,033 A | 3/1996 | Thompson | |
| 5,507,595 A * | 4/1996 | Benson | 405/43 |
| 6,150,158 A | 11/2000 | Bhide et al. | |
| 6,174,840 B1 | 1/2001 | Pauson et al. | |
| 6,223,995 B1 | 5/2001 | Evans et al. | |
| 6,237,284 B1 | 5/2001 | Erickson | |
| 2006/0003402 A1 | 1/2006 | Adris et al. | |
| 2006/0005265 A1 | 1/2006 | Bughrara et al. | |

OTHER PUBLICATIONS

Baxter, et al. Effects of elevated carbon dioxide on three montane grass species.J. Experimental Botany 1994,vol. 45, No. 3, p. 305-315.
Plant Heat-Zone Map, American Horticulture Society, 1997.
Ervin, Erik H., PhD., Corwin, Barbara S., PhD., Carbon Dioxide: culprit in bentgrass summer decline?, Golf Course Management, Apr. 1999, pp. 66-70.
Burnell, Todd B., McCarty, Bert, PhD., Gases Underground, Golf Course Management, Oct. 1999, pp. 65-69.
Huang, Bingru, PhD., Summer bentgrass decline: causes and cure, Golf Course Management, Jul. 2001, pp. 61-64.
Correspondence between Mr. Frederick "Ricky" Maier and Mr. Max Maxwell of the Country Club of Jackson, Sep. 23, 2003.
Voigt, Tom.Turfgrass Mowing. http://www.turf.uiuc.edu, Dec. 18, 2006.
The Woerner Companies. We Know Turf: Mowing. http://www.woerner.com/turf/mowing.asp, Dec. 18, 2006.
Lincoln Parish Economy. http://www.enlou.com/econ/lincoln_econ.htm, Dec. 18, 2006.
Duble, Richard L. Bentgrass. http://plantanswers.tamu.edu/turf/publications/bent/html, Dec. 18, 2006.
Vigoro Ultra Turf. Growing Beautiful Bentgrass. 2005, Spectrum Brands, Inc. http://www.vigoro.com/BrandNav/HelpfulHints/Grasses/Bentgrass.htm.
Gardner, E.H., Jackson, T.L., and Youngberg, H. Bentgrass Seed. Jan. 2000, Oregon State University, http://extension.oregonstate.edu.
Wells, Christina;Labranche,Adrienne;McCarty,Bert L.; Skipper,Horace; Can biostimulant products improve bentgrass growth? Turfgrass Trends, May 1, 2003, www.turfgrasstrends.com.
Fertilizer application rates, helping you fertilize properly, Seedland, 1999. http://www.lawnfertilizers.com/info/lawnrates.html.
Reicher, Zac and Throssel, Clark. Control of Perennial Weedy Grasses in Turf.Purdue University, Mar. 1998. http://agry.purdue.edu/turf/pubs/ay11.htm.
Range Plants of Utah, Redtop. Utah State University, 2002. http://extension.usu.edu/rangeplants/Grasses/redtop.htm.
Perennial Grasses. Purdue University.http://www.purdue.edu/dp/envirosoft/lawn/src/pest/perennial.htm, Dec. 18, 2006.

* cited by examiner

*Primary Examiner* — Fereydoun G Sajjadi
*Assistant Examiner* — Danielle Sullivan
(74) *Attorney, Agent, or Firm* — Roy Kiesel Ford Doody and Thurmon

(57) ABSTRACT

A method for substantially preventing or inhibiting summer bentgrass decline in an outdoor environment, by exposing bentgrass beds to increased amounts of atmospheric carbon dioxide. The invention is particularly well suited for use in warm climates. It is expected to be useful in a variety of bentgrass applications, such as golf greens, pastures, lawns, athletic fields, and the like. Similar applications for other cool-season grasses are anticipated as well.

33 Claims, 3 Drawing Sheets

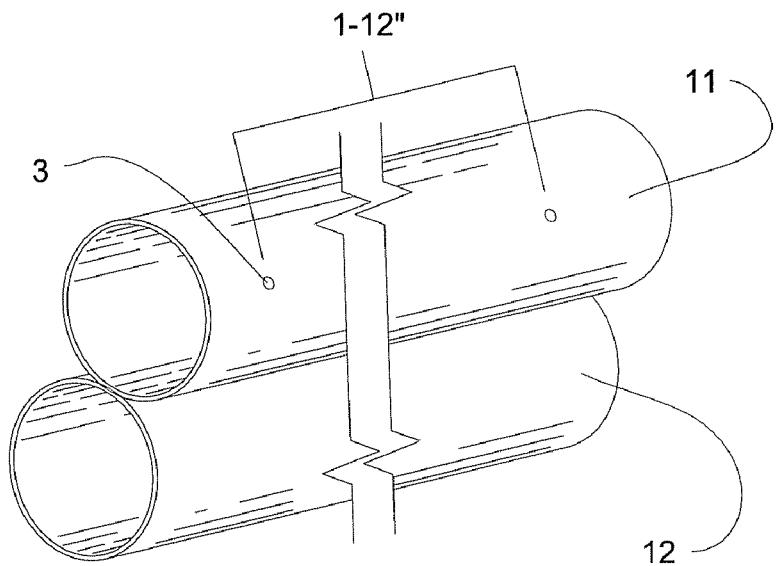
Fig. 4
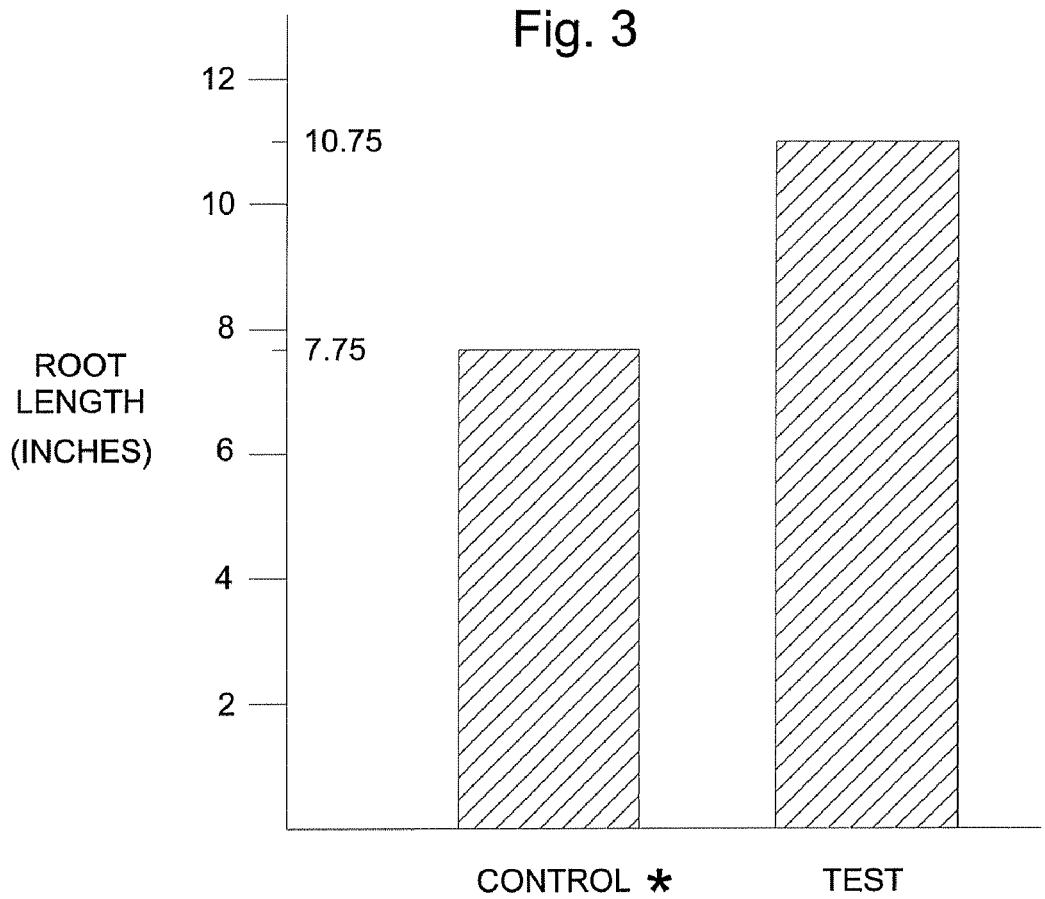

METHOD OF SUBSTANTIALLY PREVENTING OR INHIBITING SUMMER BENTGRASS DECLINE

BACKGROUND OF THE INVENTION

1. Field of the Invention

This invention relates to seasonal plant growth in general and to a method for substantially preventing or substantially inhibiting summer bentgrass decline in a warm climate, in particular.

2. Prior Art

Creeping bentgrass (*Agrostis stoloinifera* a.k.a *Agrostis palustris*) is commonly favored and utilized for pastures, lawns, athletic fields, and especially golf greens, due to its pleasing deep green appearance, and its ability to produce dense horizontal stems, called stolons, that run along the soil's surface, creating a firm carpet-like turf, ideal for putting. However, creeping bentgrass is a cool-season grass that does not grow well in high temperatures, declining in quality and decreasing in root depth in such environments. This problem is commonly referred to as summer bentgrass decline (SBD).

Consensus has not been reached as to the exact cause of SBD. There have been numerous attempts in the prior ail to discover the cause of SBD and various potential solutions have been proposed, including cooling the stems and roots of the bentgrass, aerating the soil, and adding minerals to its root zone.

One theory of the cause of summer bentgrass decline is an imbalance between the photosynthesis and respiration systems of the plant. In photosynthesis, plants absorb light and carbon dioxide from the air to produce carbohydrates. In respiration, plants consume the carbohydrates to obtain energy the plants need for growth. As a by-product of respiration, the plant emits oxygen.

In cool weather, bentgrass is able to maintain a balance between photosynthesis and respiration, which allows a sufficient amount of carbohydrates to be maintained. However, at high temperatures, the respiration rate is believed to increase while the photosynthesis rate declines. This condition is believed to be aggravated by the close mowing common on golf greens, which eliminates leaves that would have been available for photosynthesis. See, *Summer Bentgrass Decline: Causes and Cures*; Bingru Huang, PhD; GMC, July 2001, Research.

Whatever the cause of SBD, attempts to extend the use of creeping bentgrass into the south and other warmer regions have not been very successful. Because high temperatures often exceed 86° F. for extended periods in large portions of the United States, particularly the south and west, the use of bentgrass in these regions is virtually non-existent. In border states, although bentgrass is utilized, it requires a significant amount of maintenance, and green degradation in the summer months is still common.

OBJECTS OF THE INVENTION

It is an object of this invention to provide a method for substantially preventing or substantially inhibiting summer bentgrass decline in a warm climate.

It is another object of the invention to substantially prevent or inhibit summer bentgrass decline by exposing the bentgrass to elevated atmospheric concentrations of carbon dioxide.

It is yet another object of the invention to extend the use of creeping bentgrass into warmer regions.

These and other objects of the invention shall become apparent from the ensuing figures and descriptions of the invention.

SUMMARY OF THE INVENTION

A method for substantially preventing or substantially inhibiting summer decline of cool-season grasses such as bentgrass by applying carbon dioxide to the grass is disclosed. In a preferred embodiment, the carbon dioxide is supplied to an outdoor and unenclosed cool-season grass bed, via a delivery system comprising a plurality of conduits connected to a carbon dioxide source, and positioned in proximity to the cool-season grass. The method of the present invention is expected to be particularly useful in regions having daily high temperatures in excess of 86° F. for an average of at least forty-five days out of the year. In areas that experience daily high temperature in excess of 86° F. for an average of at least 30 days out of the year, the method of present invention may also be useful for spot treatments, i.e. treatments more localized in nature and lasting a shorter duration, as the bentgrass or other cool-season grass begins to exhibit signs of stress. In the preferred embodiment, the carbon dioxide content of the atmosphere around the cool-season grass is raised to a desired range, preferably from about 450 ppm to about 1000 ppm, to enhance the carbon dioxide uptake of the grass.

BRIEF DESCRIPTION OF THE FIGURES

FIG. 3 presents a graphical comparison of the root length of bentgrass treated by the method of the invention versus untreated bentgrass.

FIG. 4 is an enlarged view of a preferred embodiment of the polytubing of the preferred carbon dioxide delivery system.

DETAILED DESCRIPTION OF THE INVENTION

Creeping bentgrass is a cool-season grass that exhibits decline in regions having high temperatures. Generally speaking, when the daily high temperatures for an area exceed about 86° F. for 45 days or more out of the year, SBD is particularly severe, such that maintenance of a bentgrass bed is very difficult. Even in regions exhibiting daily high temperatures in excess of 86° F. for periods of 30 days or more, bentgrass beds may become endangered due to heat stress. Accordingly, the current invention presents an improved method to substantially prevent or inhibit summer bentgrass decline and the decline of other cool-season grasses in these regions.

The invention proposes introducing gaseous carbon dioxide over an outdoor, unenclosed bed of bentgrass, for a golf green, pasture, lawn, athletic field, or the like, such that the atmospheric carbon dioxide content around the grass is increased to an amount greater than that found in ambient air. As used herein, the terms 'outdoor' and 'unenclosed' refer to a bentgrass bed that is not situated within a facility, or a structure designed to contain same, such as hothouses or tents. However, the term 'unenclosed' is not meant to exclude any boundary markings that may be around the periphery of the bentgrass bed, such as fences, stakes, etc.

It is contemplated that gaseous carbon dioxide may be supplied to the bentgrass by a variety of delivery systems. Assuming that the bentgrass bed 6 being treated is a golf green, in one preferred embodiment of the invention, the delivery system 1 will comprise a plurality of conduits 2, in the form of polytubing 2a, such as those commercially available from the Freelin-Wade, Co. of McMinnville, Oreg.

The suggested mowing height for creeping bentgrass golf greens is about 1/10 to about 1/8 of an inch. The preferred diameter of polytubing 2a will range from about 1/16 of an inch to about 1/4 of an inch. It would obviously present a problem if polytubing 2a formed any sort of obstacle to the path of a golf ball on a putting green. Thus, the inventors contemplate burying or partially burying polytubing 2a in the bentgrass beds. In this manner, polytubing 2a can be positioned so as not to disturb the putting surface as described more fully below.

Figure 1:
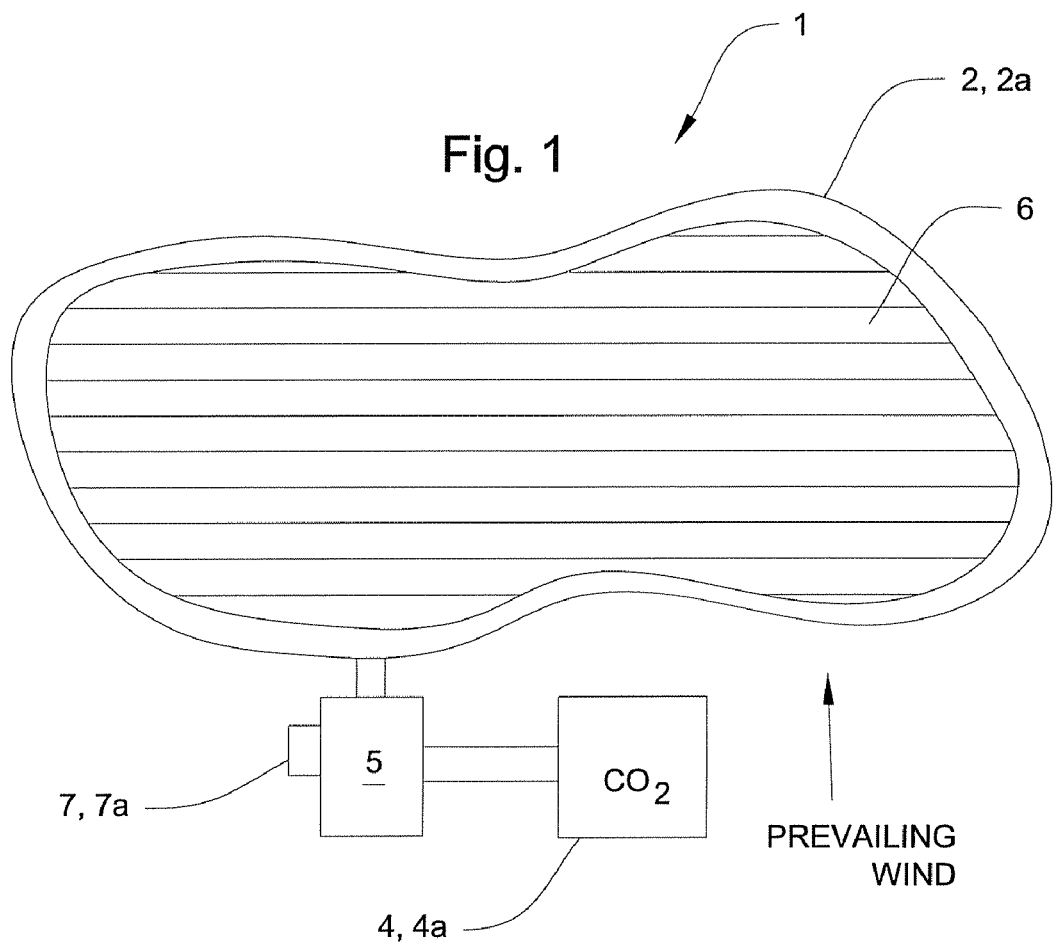
FIG. 1 is a schematic view of a preferred embodiment of a carbon dioxide delivery system.
Figure 2:
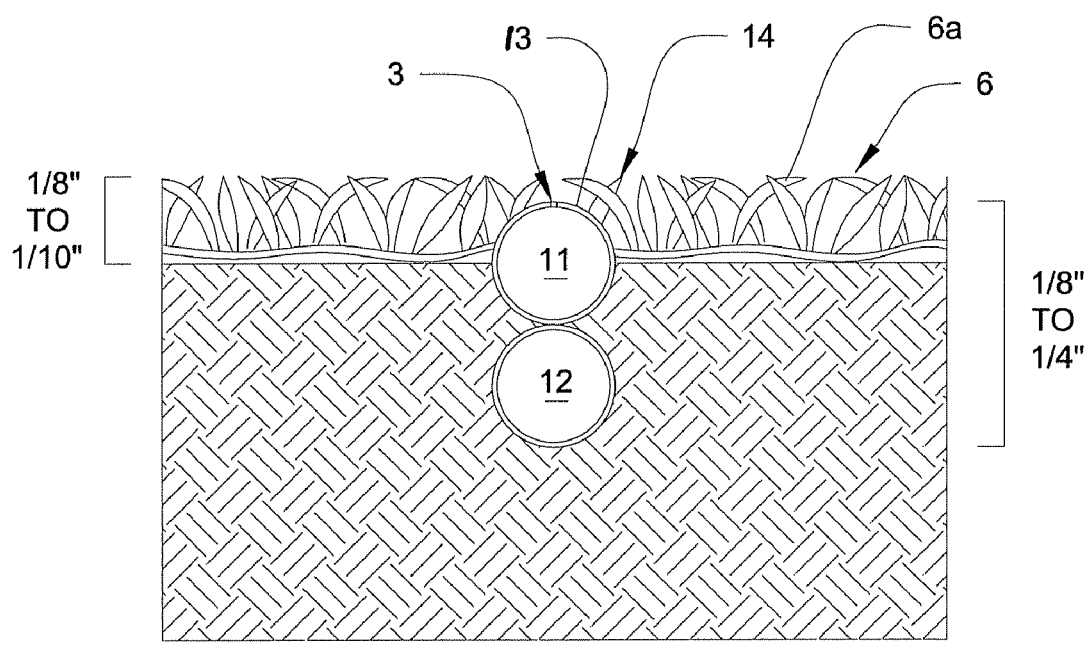
FIG. 2 is a scaled depiction of a preferred embodiment of a conduit utilized in the delivery system, depicting its preferred sizing and orientation, relative to the cool-season grass.
Figure 5:
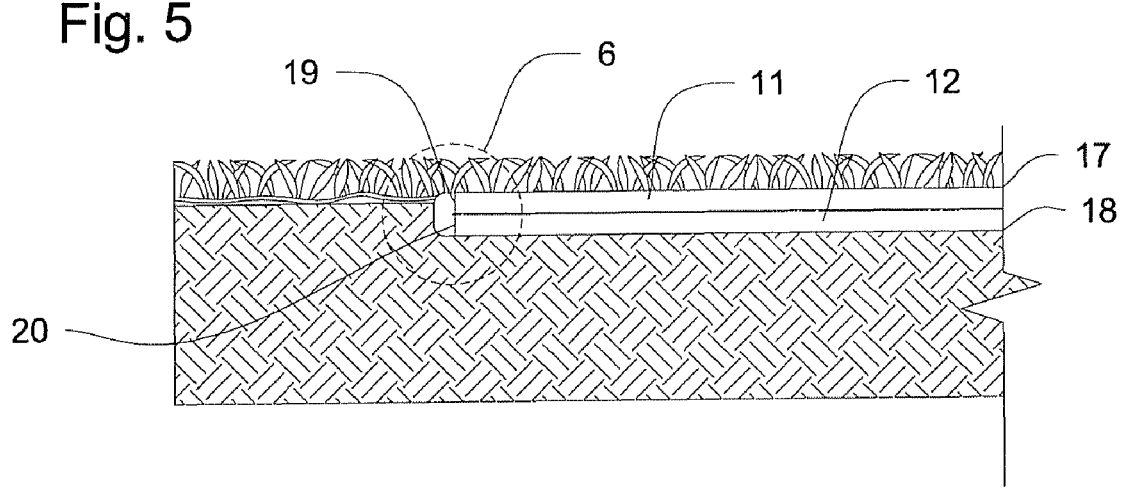
FIG. 5 is a cross-sectional view of a preferred embodiment of the polytubing of the preferred carbon dioxide system at the end of the polytubing distal from the source of the carbon dioxide.
Figure 6:
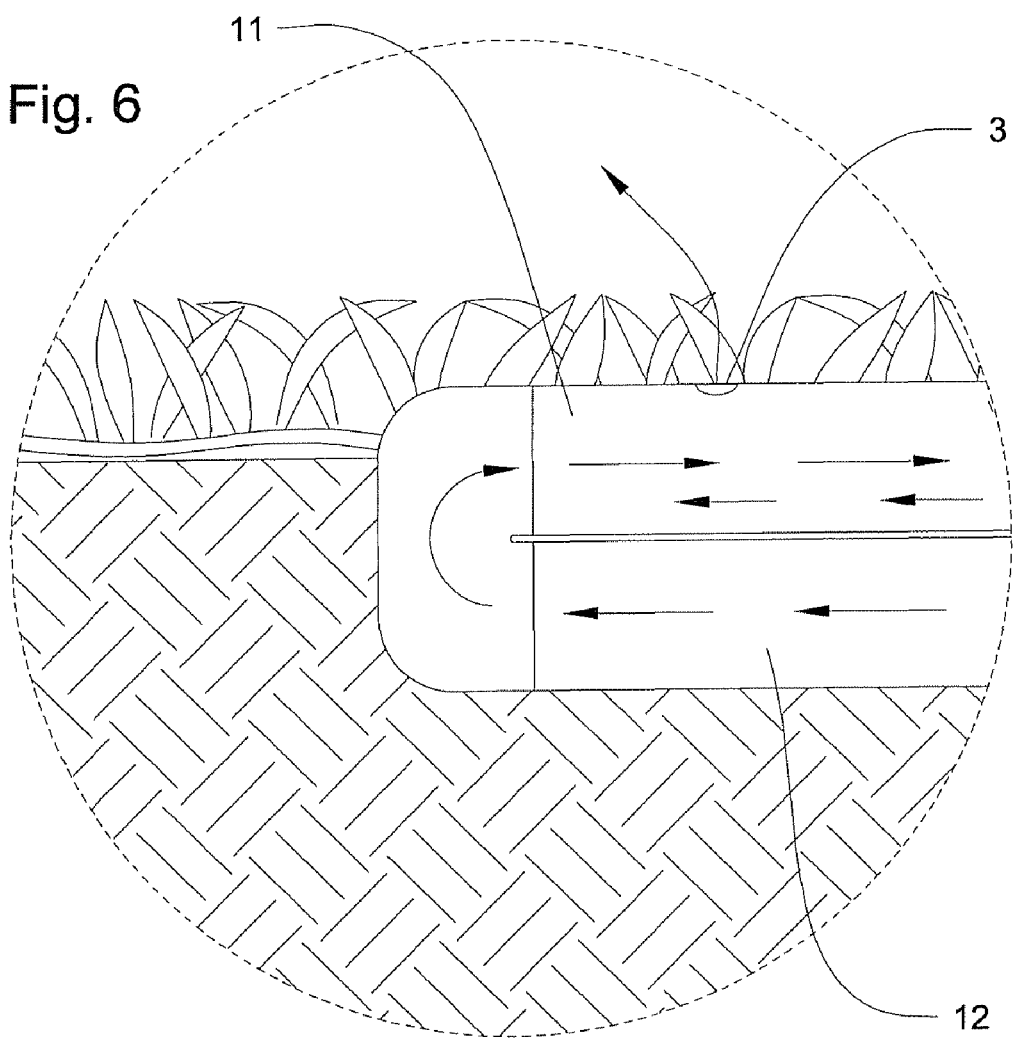
FIG. 6 is an enlarged view of the circled area of FIG. 5.

In a preferred embodiment, and as depicted in FIGS. 2, 5, and 6, a run of polytubing 2a, will take the form of a pair of stacked tubing, comprising an upper tubing 11, and a lower tubing 12. Upper tubing 11 and lower tubing 12, may be bonded together along their respective lengths, so as to form a vertical stack positioned beneath bentgrass leaves 6a. In a preferred embodiment of delivery system 1, lower tubing 12 will comprise an unperforated tubing while upper tubing 11 will preferably comprise a plurality of jets 3, each preferably having a diameter of about 0.15 mm to about 0.30 mm, drilled into the center of tubing 11 on approximately 1 to 12 inch centers, as depicted in FIG. 4. Jets 3 may be formed in tubing 11 using a Dremel brand or other similar rotary tool mounted in a drill press and fitted with a bit of the appropriate size.

Tubing 11 and 12 will preferably be connected to a source of carbon dioxide gas 4*a* comprising a cylinder of pressurized carbon dioxide 4 via a manifold 5 at their respective ends 17, and 18, and will further be fluidly connected to each other either along their length or preferably at their respective ends 19 and 20, opposite manifold 5. In the preferred embodiment, the carbon dioxide gas will be applied at one end 18 of lower tubing 12, at both ends, 17 and 19, of upper tubing 11, and will be released upwardly toward the bentgrass leaves 6*a* through jets 3. See FIG. 6. The utilization of this type of double tubing delivery system 1 is advantageous because it effectively feeds upper tubing 11 at both ends. This will help maintain the gas pressure across the length of upper tubing 11, keeping the flow of gas at a desired velocity and effectively allowing tubes 11 and 12 to serve longer distances.

In a further preferred embodiment, and as depicted by FIG. 2, bentgrass 6 will be cut at a substantially uniform height. Upper tubing 11 and lower tubing 12 will be positioned so that the top edge 13 of upper tubing 11 is approximately even with, or just below the level at which the bentgrass 6 is cut. To achieve this, small trenches are cut into the soil of bentgrass bed 6. Tubings 11 and 12 are then positioned in the trenches such that the top edge 13 of upper tubing 11 protrudes the desired distance above the soil surface. Although similar results could be obtained with a smaller trench by using a single tubing 11 without lower tubing 12, a double tubing delivery system 1 will also help maintain tipper tubing 11 in a stable orientation, with its jets 3 facing in the preferred direction, directly upward.

In a further preferred embodiment of delivery system 1, and as depicted by FIG. 1, one run of polytubing 2*a* will be installed along the perimeter of the area to be treated, with other individual runs of tubing 2*a* installed on 5 to 10 foot centers, and most preferably on centers of approximately 6 feet, in a parallel formation, throughout the area. In a further preferred embodiment, the runs of polytubing 2*a* will be installed in lines ruining across bentgrass bed 6, the lines being generally perpendicular to the prevailing wind in the area, such that the wind will move the gas into the areas between the runs of polytubing 2*a*, to provide for an even distribution of the gas across bentgrass bed 6.

In a further preferred embodiment, delivery system 1 will be provided with a mechanism 7 to modulate the flow of the carbon dioxide gas. For testing purposes, this will preferably be accomplished by connecting each run of tubing 2*a* to a pressure regulator 7*a*, such that each run of tubing 2*a* can be pressurized at selected levels to control the flow rate of the gas. However, in the commercial embodiment, the inventors contemplate that a run of tubing 2*a* at the perimeter of bentgrass bed 6 will be pressurized and that the other runs will be fed gas via the run of tubing 2*a* at the perimeter.

If the pressure is high enough, the flow will exit jets 3 at sonic velocity. Thus, in a preferred method of operation, the delivery system of the present invention is pressurized at approximately 13 pounds per square inch (psi), to provide for a choked jet condition, at which sonic velocity is achieved—i.e., the carbon dioxide gas is released into the atmosphere at the speed of sound. The gas exiting polytubing 2*a* at the speed of sound will in turn create a shock wave. This will result in the rapid mixing of the carbon dioxide with the surrounding air to provide a fairly uniform concentration of the gas across the treated area. Under choked jet conditions, increasing the pressure will increase the volume of the gas delivered such that the carbon dioxide concentration can be raised to the desired level; however, increasing the pressure will not increase the speed at which gas exits jets 3.

In a further preferred embodiment of the invention, carbon dioxide will preferably be supplied to the bentgrass during the daylight hours; however, it is contemplated that carbon dioxide could also be supplied during non-daylight hours, provided that appropriate lighting is provided to allow photosynthesis to occur. In a further preferred embodiment, the delivery system pressure will be adjusted to maintain an elevated level of carbon dioxide above that of ambient atmospheric conditions, that is, above about 0.038% carbon dioxide (380 ppm). An elevated carbon dioxide content ranging from about 450 ppm to about 1000 ppm will be maintained. Although higher concentrations could be used, it is expected that beneficial effects will diminish above this upper concentration. More particularly, an optimum carbon dioxide concentration of about 700 ppm is desired. Treatment in this fashion is expected to be useful, primarily in regions where the daily high temperature exceeds about 86° F. for an average of at least 45 days or more out of the year. Referring to the American Horticultural Society's Plant Heat Zone Map, which is hereby incorporated by reference, such areas are exemplified by Regions 6-12. It is further contemplated that 'spot treatments' utilizing the method of the present invention may also be useful for bentgrass beds located in regions where the daily high temperature exceeds about 86° F. for an average of at least 30 days out of the year, shown as Region 5 on the above referenced map. It will be appreciated that changes in climate and prevailing weather patterns may effect the regions where the invention is needed.

Alternate delivery systems capable of achieving the purpose of this invention, may also be suitable. For example, in one alternative embodiment, an overhead gas application system, utilizing horizontal pipes to discharge carbon dioxide into the air above the bentgrass, may be utilized. In another alternative embodiment, carbon dioxide may be supplied by allowing solid dry-ice to sublimate above the bentgrass. Another possible delivery system comprises dissolving carbon dioxide in an aqueous solution and spraying the solution on the grass.

It should be noted that the method of the present invention, although discussed in the context of creeping bentgrass (*Agrostis stolonifera*), may also be applicable to other species/varieties of grasses within the *Agrostis* genera, such as velvet bentgrass, (*Agrostis canina*), colonial bentgrass (*Agrostis capillaris*), and redtop (*Agrostis gigantea*). Furthermore, it is contemplated that the methodology of the present invention may also be applicable to other types of cool-season grasses that exhibit summer stress in warmer temperatures. Non-limiting examples include species/varieties within the *Festuca* genera; species within the *Poa* genera, such as annual bluegrass (*Poa annua*), Kentucky bluegrass, (*Poa pratensis*), and rough bluegrass (*Poa trivialis*); and species within the *Lolium* genera, such as annual ryegrass (*Lolium annua*) and perennial ryegrass (*Lolium perenne*).

The present invention confers a significant advantage, as by substantially preventing or inhibiting summer bentgrass decline, it will be possible to extend the use of creeping bentgrass into warm climate regions for desired applications, something that has not been possible or economically feasible to date.

The preferred embodiments of the present invention are further described by reference to the following examples. The examples are offered by way of illustration and are not intended to limit the invention in any manner.

Example 1

Methodology

In the fall, the inventors established an outdoor bed of bentgrass in Lincoln Parish, Louisiana. This region has an average daily high temperature in July and August of 93° F. The bed of bentgrass established by the inventors was a randomized block comprising three varieties of Creeping bentgrass: Penn A1 (Agrostis stolonifera 'Penn A-1'), Penn A2, (Agrostis stolonifera 'Penn A-2') and Penn A4 (Agrostis stolonifera 'Penn A-4'). The bentgrass bed was maintained over the winter. During the following July and August, the inventors constructed a conduit system through which carbon dioxide was pumped over a portion of the bentgrass bed (test zone). The conduit system comprised a plurality of hollow PVC pipes, each pipe having an approximate length of 72 inches and an approximate diameter of ¾ of an inch. Several of the pipes were affixed to each other to form the perimeter of a support platform having a rectangular shape. The remaining pipes were arranged in a parallel fashion and affixed within the support platform. A plurality of jets, having an approximate diameter of 3/16 of an inch, were drilled into each pipe. The support platform was positioned above the bentgrass bed at an approximate height of 10 inches. A corner of the support platform was connected to a cylinder of pressurized carbon dioxide via a hose. The carbon dioxide was delivered to the conduit system via a forced air blower. Another portion of the bentgrass bed was designated as the control zone and remained untreated. All other variables, i.e. wear on the bed, fertilization rate, (nitrogen was applied at a rate of about ½ pound per 1000 square feet per month), mowing practices (the grass was kept mowed at a height of 1/10 to 1/8 of an inch), etc. were kept constant. An elevated atmospheric carbon dioxide concentration of about 700 ppm was maintained over the test zone from daylight until dark throughout the months of July and August, while the control zone was kept at ambient atmospheric conditions, at a carbon dioxide concentration of about 380 ppm. The carbon dioxide concentrations in both zones were monitored via a standard, commercially available gas analyzer. At the end of August, both the treated and non-treated areas of the bentgrass were assayed visually for quality and also measured for root-depth.

Results

The bentgrass in the test zone did not experience a loss in quality, remaining lush and green and displaying good shoot and root growth, all summer. On the other hand, the untreated zone did experience a serious quality loss, displaying brown dry spots and broad patches of dead grass, with at least thirty percent of the control portion being dead. Additionally, substantial differences in the length of the roots of the bentgrass exposed to the carbon dioxide were observed. A sample root taken from the test zone had a length of approximately 10.75 inches, while a sample root taken from the control zone had a length of approximately 7.75 inches. See FIG. 3. However, it should be noted that the root sample of the control area was taken from the healthiest area of the control zone, as the grass in substantial portions of the control zone was dead and thus devoid of living roots. The results indicated that elevated atmospheric levels of carbon dioxide could substantially prevent or inhibit summer bentgrass decline While the invention has been described in terms of its preferred embodiment, other embodiments will be apparent to those of skill in the art from a review of the foregoing. Those embodiments as well as the preferred embodiments are intended to be encompassed by the scope and spirit of the following claims.

We claim:

1. A method for inhibiting summer bentgrass decline in a warm climate comprising applying gaseous carbon dioxide to the stomata of bentgrass in an unenclosed outdoor bed in a location having an average of at least thirty days per year in which the daily high temperature exceeds eighty-six degrees Fahrenheit, wherein the gaseous carbon dioxide is applied in an amount sufficient to increase the atmospheric content of carbon dioxide proximate to the bentgrass stomata to a level of at least 450 parts per million.

2. A method for inhibiting summer bentgrass decline according to claim 1, wherein the bed of bentgrass is on a golf putting green.

3. A method for inhibiting summer bentgrass decline according to claim 1, wherein the gaseous carbon dioxide is applied to the bentgrass during daylight hours.

4. A method for inhibiting summer bentgrass decline according to claim 1, wherein the gaseous carbon dioxide is applied in an amount sufficient to increase the atmospheric content of carbon dioxide proximate to the bentgrass stomata to a level ranging from about 450 parts per million to about 1000 parts per million.

5. A method for inhibiting summer bentgrass decline according to claim 1, wherein the gaseous carbon dioxide is applied in an amount sufficient to increase the atmospheric content of carbon dioxide proximate to the bentgrass stomata to about 700 parts per million.

6. A method for inhibiting summer bentgrass decline according to claim 1 wherein the unenclosed outdoor bed is in a location having an average of at least forty-five days per year in which the daily high temperature exceeds eighty-six degrees Fahrenheit.

7. A method for inhibiting summer bentgrass decline according to claim 1, wherein a gas delivery system is utilized to apply the carbon dioxide to the bentgrass.

8. A method for inhibiting summer bentgrass decline according to claim 7, wherein the gas delivery system comprises a source of carbon dioxide gas and a conduit system in fluid communication with the source of carbon dioxide to transmit the gas to the bentgrass.

9. A method for inhibiting summer bentgrass decline according to claim 7 wherein the gas delivery system is configured to release the carbon dioxide to the bentgrass at sonic velocity.

10. A method for inhibiting summer bentgrass decline according to claim 7, wherein the delivery system comprises a plurality of conduits containing jets.

11. A method for inhibiting summer bentgrass decline according to claim 10, wherein the conduits comprise polytubing.

12. A method for inhibiting summer bentgrass decline according to claim 11, wherein substantially all of said polytubing has a diameter ranging from about 1/16 to about 1/4 of an inch.

13. A method for inhibiting summer bentgrass decline according to claim 11, wherein said bentgrass is cut to a substantially uniform level.

14. A method for inhibiting summer bentgrass decline according to claim 13, wherein said polytubing is positioned below the level at which said bentgrass is cut.

15. A method for inhibiting summer bentgrass decline according to claim 14, wherein said polytubing comprises a pair of vertically stacked tubing.

16. A method for inhibiting summer bentgrass decline according to claim 15, wherein the pair of vertically stacked tubing comprises an upper tubing and a lower tubing.

17. A method for inhibiting summer bentgrass decline according to claim 16, wherein the upper tubing comprises a plurality of jets.

18. A method for inhibiting summer bentgrass decline according to claim 17, wherein the jets have a diameter between about 0.15 mm and about 0.30 mm.

19. A method for inhibiting summer bentgrass decline according to claim 17, wherein said gas delivery system further comprises a cylinder of carbon dioxide connected to the polytubing via a manifold.

20. A method for inhibiting summer bentgrass decline according to claim 19, wherein the upper tubing and the lower tubing are each fluidly connected to the cylinder at a first end and are further fluidly connected to each other at a second end opposite the cylinder.

21. A method for inhibiting summer bentgrass decline according to claim 20 wherein the upper tubing and the lower tubing are positioned in a trench in the bentgrass bed.

22. A method for inhibiting summer bentgrass decline according to claim 19, wherein at least some of the polytubing is installed along at least a portion of the perimeter of the area of the bentgrass to be treated.

23. A method for inhibiting summer bentgrass decline according to claim 19 wherein a plurality of the polytubing is installed in substantially parallel runs.

24. A method for inhibiting summer bentgrass decline according to claim 10, wherein the delivery system of the present invention is pressurized to approximately thirteen pounds per square inch whereby the delivery system releases the carbon dioxide to the bentgrass at sonic velocity.

25. A method for inhibiting the decline of a cool-season grass that exhibits summer stress in warmer temperatures comprising applying gaseous carbon dioxide to the stomata of the cool-season grass in an unenclosed outdoor bed wherein the gaseous carbon dioxide is applied in an amount sufficient to increase the atmospheric content of carbon dioxide proximate to the cool-season grass stomata to a level of at least about 450 parts per million.

26. A method for inhibiting cool-season grass decline according to claim 25, wherein the outdoor bed is in a location having an average of at least thirty days per year in which the daily high temperature exceeds eighty-six degrees Fahrenheit.

27. A method for inhibiting cool-season grass decline according to claim 25, wherein the grass is from the Agrostis genera.

28. A method for inhibiting cool-season grass decline according to claim 25, wherein the grass is from the Poa genera.

29. A method for inhibiting cool-season grass decline according to claim 25, wherein the grass is from the Festuca genera.

30. A method for inhibiting cool-season grass decline according to claim 25, wherein the grass is from the Lolium genera.

31. A method for inhibiting cool-season grass decline according to claim 25, wherein the gaseous carbon dioxide is applied to the cool-season grass during daylight hours.

32. A method for inhibiting cool-season grass decline according to claim 25, wherein the gaseous carbon dioxide is applied in an amount sufficient to increase the atmospheric content of carbon dioxide proximate to the cool-season grass stomata to a level ranging from about 450 parts per million to about 1000 parts per million.

33. A method for inhibiting cool-season grass decline according to claim 25, wherein the gaseous carbon dioxide is applied in an amount sufficient to increase the atmospheric content of carbon dioxide proximate to the cool-season grass stomata to about 700 parts per million.

* * * * *